(12) United States Patent
Schneider et al.

(10) Patent No.: US 10,046,327 B2
(45) Date of Patent: Aug. 14, 2018

(54) HEATABLE TWEEZERS, AND CHARGING DEVICE FOR THE TWEEZERS

(71) Applicant: pfm medical ag, Cologne (DE)

(72) Inventors: Erwin Schneider, Nussloch (DE); Steffen Kraus, Sandhausen (DE)

(73) Assignee: pfm medical ag, Cologne (DE)

( * ) Notice: Subject to any disclaimer, the term of this patent is extended or adjusted under 35 U.S.C. 154(b) by 0 days.

(21) Appl. No.: 15/302,577

(22) PCT Filed: May 22, 2015

(86) PCT No.: PCT/DE2015/200322
§ 371 (c)(1),
(2) Date: Oct. 7, 2016

(87) PCT Pub. No.: WO2015/180722
PCT Pub. Date: Dec. 3, 2015

(65) Prior Publication Data
US 2017/0036211 A1 Feb. 9, 2017

(30) Foreign Application Priority Data

May 30, 2014 (DE) ........................ 10 2014 210 298

(51) Int. Cl.
*G01N 1/10* (2006.01)
*B01L 9/00* (2006.01)
(Continued)

(52) U.S. Cl.
CPC ................ *B01L 9/50* (2013.01); *A61B 17/30* (2013.01); *B01L 7/00* (2013.01); *B01L 9/00* (2013.01);
(Continued)

(58) Field of Classification Search
CPC ....................................................... B01L 9/50
See application file for complete search history.

(56) References Cited

U.S. PATENT DOCUMENTS 5,556,563 A 9/1996 von der Heyde et al.
6,235,027 B1 5/2001 Herzon
(Continued)

FOREIGN PATENT DOCUMENTS

CN 204255733 U 4/2015
DE 3002088 A1 7/1981
(Continued)

OTHER PUBLICATIONS

The International Bureau of WIPO, International Preliminary Report on Patentability (English translation of ISA's Written Opinion) for Application No. PCT/DE2015/200322, dated Dec. 6, 2016, 10 pages, Switzerland.
(Continued)

*Primary Examiner* — Jyoti Nagpaul
(74) *Attorney, Agent, or Firm* — Alston & Bird LLP (57) ABSTRACT

Tweezers, in particular for handling histological preparations, preferably thin tissue specimens, with two limbs connected elastically at one end, and with tips formed at the other, free end of the limbs and together forming an engagement area, wherein a central area serves for holding and actuating the limbs in order to bring the tips into contact with each other, are characterized in that the tips and/or the connection area of the limbs are designed as a housing with a storage medium for storing energy, and in that the storage medium directly or indirectly heats the engagement area or the tips to a predefined temperature.

23 Claims, 8 Drawing Sheets

(51) Int. Cl.
  *A61B 17/30* (2006.01)
  *B01L 7/00* (2006.01)
  *A61B 17/00* (2006.01)
  *A61B 10/06* (2006.01)

(52) U.S. Cl.
  CPC ..... *A61B 10/06* (2013.01); *A61B 2017/00473* (2013.01); *B01L 2300/023* (2013.01); *B01L 2300/025* (2013.01); *B01L 2300/1827* (2013.01)

(56) References Cited

U.S. PATENT DOCUMENTS

| | | |
|---|---|---|
| 2005/0121495 A1 | 6/2005 | Yokoyama |
| 2006/0095098 A1* | 5/2006 | Shanks ................ A61N 5/0616 607/89 |
| 2011/0046620 A1 | 2/2011 | Lewandowski et al. |
| 2011/0278942 A1 | 11/2011 | Eckhoff et al. |

FOREIGN PATENT DOCUMENTS

| | | | |
|---|---|---|---|
| DE | 4305057 A1 * | 8/1994 | ................ B01L 9/50 |
| DE | 4305057 A1 | 8/1994 | |
| DE | 102004031927 A1 | 1/2006 | |
| WO | WO 2004/008907 A1 | 1/2004 | |

OTHER PUBLICATIONS

International Searching Authority, International Search Report and Written Opinion for International Application No. PCT/DE2015/200322, dated Sep. 30, 2015, 12 pages, European Patent Office, Netherlands.

European Patent Office, Communication in accordance with Article 94 (3) EPC for Application No. 15736392.0, dated Aug. 3, 2017, 5 pages, Netherlands.

European Patent Office, Communication in accordance with Article 94 (3) EPC for Application No. 15736392.0, dated Feb. 2, 2017, 5 pages, Netherlands.

\* cited by examiner

HEATABLE TWEEZERS, AND CHARGING DEVICE FOR THE TWEEZERS

CROSS REFERENCE TO RELATED APPLICATIONS

This application is a national stage application, filed under 35 U.S.C. § 371, of International Application No. PCT/DE2015/200322, filed May 22, 2015, which claims priority to German Application No. 10 2014 210 298.7, filed May 30, 2014, the contents of both which as are hereby incorporated by reference in their entirety.

BACKGROUND

The invention relates to tweezers, in particular for handling histological preparations, preferably thin tissue specimens, with two legs connected elastically at one end, and with tips formed at the other free end of the legs, which together form an engagement area, wherein a central area serves for holding and actuating the legs in order to bring the tips into an arrangement next to one another or contact with each other.

Tweezers generally means a tool that serves for gripping small objects. Tweezers usually consist of two legs joined to one another which can be made of metal, plastic, fiberglass-reinforced plastic or ceramic. The legs, or rather their tips, can be moved toward each other by means of slight pressure. When the tips of the tweezers make contact, the tweezers are closed and grasp.

The term "tip" is to be understood in its broadest sense. It concerns the free end of the two legs, which may be pointed in the literal sense of a tip, but also round, polygonal or some other shape. The legs of the tweezers can have a variety of cross-sections. They can be straight or curved. The inside of the tips can also be grooved to engage the particles more effectively.

Histology is concerned with the study of biological samples and should be understood as a branch of medicine or biology, and more precisely a branch of anatomy or pathology. The histologist examines tissue samples, manufacturing micrometer-thin, usually colored tissue sections and examining them under the microscope. The fine, small tissue sections need to be handled in order to prepare them, embed them and/or position them on a microscope slide. Tweezers with suitably shaped tips are customarily used for handling them.

In order not to damage the delicate tissue samples, they may come into contact only with suitably temperature-controlled tools/handling devices. If the handling device, e.g. the tweezers, are a metallic object with a high thermal conductivity, they tend to rapidly assume the temperature of a cold tabletop, for instance. This is harmful to the samples. The remedy for this problem so far has been to place the tweezers on a hotplate and then use the tempered tweezers. This is cumbersome and, moreover, does not guarantee a homogeneous tweezer temperature. Furthermore, the tweezers cool off quickly owing to their lack of sufficiently great mass. It is not possible to reproducibly handle biological samples in this manner.

BRIEF SUMMARY

It is therefore the object of the present invention to propose tweezers of the generic type with which tissue samples can be handled in an ideal manner. In addition, a device for providing such tweezers will also be specified.

The object mentioned above is achieved by the features of the claims provided herein.

The tweezers according to the invention are characterized in that the tips and/or the joint region of the legs are designed as a housing with a storage medium for storing power, and that the storage medium directly or indirectly heats the engagement region, i.e. the tips, to a predetermined temperature.

The invention recognizes that it is advantageous to provide tweezers with a predetermined, in other words specifiable, constant temperature. To that end, the tweezers are furnished with a storage medium for storing power, said storage medium directly or indirectly heating the engagement region, i.e. the tips, of the two legs to a predetermined temperature and maintaining this temperature.

The storage medium can be integrated into the legs and/or the joint region of the legs at one end thereof, making it possible to use the entire available volume. Accordingly, the legs and the joint region, i.e. the entire body of the tweezers, can be constructed as a housing with the storage medium located inside the housing.

The storage medium can, for instance, be a heat store which is heated through direct thermal coupling. The housing has a thermally insulating character, so that the heat is expelled almost exclusively via the tips. Accordingly, the heat storage capacity of the material can be optimally exploited.

In a particularly advantageous development of the invention, the storage medium is an electrical power store which feeds an electrical heating unit which acts upon the engagement region, i.e. the tips. It is also expedient when the heating unit is a resistance heater which is in thermally conductive contact with the engagement region, i.e. the tips.

The resistance heater can comprise a special heating element, for instance a heating wire, heating coil, heating jacket, heating pad or heating cartridge. The ends of the tips are inserted into the heating element, creating thermally conductive contact between the heating element and the tips.

The electrical power store can be constructed as a battery or capacitor or capacitor arrangement. What is essential is that electrical power is stored, similarly to an electric toothbrush, where the power storage device, specifically a battery, is inductively charged when placed in a charging station. Regarding the construction of such a charging station, the features of the device claims will be laid out herein below.

According to a further advantageous embodiment, a control is provided for heating the engagement region to a predetermined or predeterminable, i.e. settable, temperature. This control can comprise a kind of power management, namely in order to realize an optimal tweezer temperature control for an optimally long time period with a predetermined amount of power. The temperature of the tips can conceivably be adjustable within a given range, with the control enabling the optimal use of the available power. To this end, it is essential that the heated region actually be concentrated only at the tips, so that they can be held at body temperature, for instance, using the lowest possible amount of power. The tips should be made of a metal with a high thermal conductivity and a large heat storage capacity. It is also conceivable for the tips to be coated, preferably with a thermally conductive material such as titanium or a titanium alloy, regardless of the base material. The coating material should be hard and robust, namely in order to reduce wear and tear. The tips can be designed more robust this way.

It is also expedient that the legs or the housing thereof are produced from plastic and/or ceramic. As mentioned above, the housing should have thermally insulating properties. On the exterior, measures can be taken to improve the haptics of the housing, or respectively the legs, such as by providing knobs, grooves, or the like, namely measures which facilitate handling.

It must be noted here that the tweezers constructed as described above must contain all the elements necessary for power transmission and heating of the tips, in a manner similar to an electric toothbrush with regard to kinetics. The battery is usually charged inductively just as with the electric toothbrush. The further description of those electrical/electronic elements and modules can be dispensed with; reference is made to similarly functioning devices.

The engagement region forming the tips of the tweezers, i.e. the tips, can be exchangeable in pairs so that the tweezers are universally usable. The exchangeable free ends of the legs, namely the tips, can be connected to the leg stumps by friction and/or interlockingly, in particular via a plug connection, snap connection, screw connection, or bayonet connection. Easy tip exchange simplifies handling significantly. For instance, flat "tips" can be effortlessly replaced with claw-shaped tips of any shape as needed. The tweezers can also be repurposed as a cutting/punching device by changing the tips appropriately.

As mentioned above, in one tweezer configuration, similarly to an electric toothbrush, an electrical charging station is provided, particularly for inductively charging the power storage device provided in the tweezer body. This can automatically supply an integral heating device with electrical power. An external power supply can also directly supply the internal, i.e. integral, heating device, namely when the tweezers are situated in a corresponding charging station.

It is also conceivable for a switch to be provided at a tweezer leg, for instance, for the purpose of activating the heating device, so that heating begins when the tweezers are turned on.

With reference to a device, the above-stated objective is attained by the features of the broadest device-based claim provided herein. According to this claim, a device for providing at least one usable pair of tweezers according to the embodiments described above is characterized by a housing which forms a station and, constructed in the housing, preferably on the top, a region for insertion/placement/attachment, which serves for positioning and charging the tweezers. The tweezers are preferably charged in an upright position, i.e. vertically, similarly to an electric toothbrush. It is also conceivable for the tweezers to be placed in a charging bay constructed in the housing, in which case the inductive coupling occurs in the known manner given such positioning.

With regard to working continuously with temperature-controlled tweezers, it is also expedient when the housing comprises two regions for inserting/placing/attaching two independent pairs of tweezers. Thus the first pair of tweezers can be used in a fully charged and heated condition until the electrical power for heating the tips and holding them at a predetermined temperature level is used up. In order to determine when that happens, the temperature in the tips can be detected by means of a temperature sensor which emits a signal via a corresponding processor directly to the tweezers or over a contactless connection via the station. When the tweezer battery charge status is no longer sufficient, the user can place it in the charging station and use the second pair of tweezers. The first pair of tweezers will recharge during this time. Special electronics for rapid charging can be provided.

As already stated above, the insertion/placement/attachment regions are constructed as inductively functioning charging stations, in which case the tweezers can comprise a hermetic housing which eliminates as far as possible the risk of damage due to improper handling. Accordingly, the station housing is equipped with a continuous surface regardless of the respective contour, so that the station does not pose any risks either. In addition, this design allows the surfaces to be cleaned much more easily.

As described above, the tips of the respective tweezers are exchangeable, preferably in pairs. Accordingly, it is expedient that the housing comprises a plurality of receptacles, particularly insertion openings or attachment pins, for providing pairs of tips with a variety of shapes. They can be provided adjacent one another either in an upright position, sticking out, or recumbent position, namely in duplicate, as long as the station comprises two pairs of tweezers.

It is also expedient that the tips/pairs of tips are provided in the heated and temperature-controlled condition. For the purpose of heating the receptacles, or respectively the pairs of tips located therein, a special heating device can be provided, which is either constructed as a resistance heater or inductively connected directly to the tip material. This measure benefits the power management of the power storage device in the tweezers, especially since it is unnecessary to heat up a pair of replacement tips from a low temperature at which they are provided to a temperature corresponding to body temperature, for instance.

The same applies to the provision of the tweezers themselves. As long as the tweezers are in the charging station, the tip temperature control process can already be activated, so that the tweezers are provided with temperature-controlled tips. All these functions can be activated by means of a control panel, preferably a touch panel, which is preferably allocated to the display. Film-protected switches which are integrated into the display area can also be provided.

As mentioned above, the housing comprises a display, which is preferably integrated into a front, upwardly inclined region of the housing. The display indicates the operating mode of the station and/or the charge status of the tweezers.

In a particularly refined manner, the connection between the station and the respective tweezers can be a wireless connection, preferably a Bluetooth connection, a connection via high-frequency signals, or a connection over a WLAN network, in which case integration in a computer system is also possible. It is also conceivable for the station to be controlled by means of an organizer with the aid of a separate program in the form of a so-called app.

The charge status/operating mode of the tweezers can conceivably also be displayable and potentially also communicable to the user visually and/or acoustically via the station by means of the display provided in the housing there. That way, the user has the ability while at the station to determine, or at least estimate, how long he can continue to use the tweezers with sufficient temperature control. If necessary, he will then return the tweezers to the charging station and use the second pair of tweezers which is being stored.

Through the interaction of the inventive device described above and the inventive tweezers described above, the heating of the tweezers, in which an internal heating device as well as a battery for storing electrical power are located, can proceed as follows:

The tweezers are located in the charging cradle, i.e. the insertion/placement/attachment region, and positioned there accordingly. In this condition the device, which holds at least one pair of tweezers, is switched on. As long as they are properly situated in the charging station, the tweezers are supplied directly with electrical power, and the electrical power, i.e. the current, does not flow from the battery of the tweezers. Rather, while the battery is bypassed, or while the battery is expediently charging, the tweezers are supplied with current directly, or more precisely the internal heating device of the tweezers is supplied with current directly, so that the tweezers, in particular their tips, are brought to operating temperature. The battery charging process occurs simultaneously.

When the tweezers are removed from the charging station, they, in particular their tips, are temperature-controlled by means of the internal battery of the tweezers.

As soon as the electrical power of the internal battery is used up, for instance after a period of 30 minutes, an acoustic signal or a visual signal such as a warning lamp is triggered, which notifies the user that the tweezers need to be placed in the charging station of the device again in order to recharge the battery. When the tweezers are back in the charging station again, the process repeats itself as described above; i.e., the internal heating device is supplied with power directly, and the tweezer tips are heated while the battery charges.

When two charging stations and correspondingly at least two pairs of tweezers are provided, the second pair of tweezers is available "charged"; i.e., the tweezer tips are at operating temperature, and the second tweezers' battery is "full". This second pair of tweezers can be used while the first pair of tweezers undergoes the charging process—the heating of the tweezer tips through a direct power supply and the charging of the battery.

During the charging process the device, i.e. the charging station, takes over the power supply until the desired temperature is reached in the tweezer tips. If necessary the tweezers can then be exchanged, so that the provision of at least two tweezers enables continuous work.

It is generally also conceivable for the temperature of the tweezers, i.e. their tips, to be controlled by means of the charging station directly without an internal heating device being provided in the tweezers. In this case, given the provision of a corresponding heat accumulator, the tweezers would be charged thermally and could be used for as long as the heat accumulator supplied sufficient heat to the tweezer tips to keep them at operating temperature. An alarm could be emitted when the temperature fell below the operating temperature, so that the first pair of tweezers, whose heat accumulator was no longer sufficiently "full", could be exchanged for the second pair of tweezers, which was thermally charged up.

BRIEF DESCRIPTION OF THE FIGURES

There are various options for developing and implementing the teaching of the present invention in an advantageous manner. For this purpose, reference is made first to the claims subordinate to Claim 1, and secondly, to the following description of an exemplifying embodiment of the invention using the drawings. In the context of the explanation of the preferred exemplary embodiment of the invention and the drawings, other generally preferred embodiments and further developments of the teaching are explained as well. The drawings show:

DETAILED DESCRIPTION OF VARIOUS EMBODIMENTS

The figures show an exemplary embodiment of the device according to the invention for providing two pairs of tweezers 1 according to the invention and variably shaped tips 2 intended to be exchanged. The tips 2 are stocked, in other words made available for exchange, in pairs.

Figure 1:
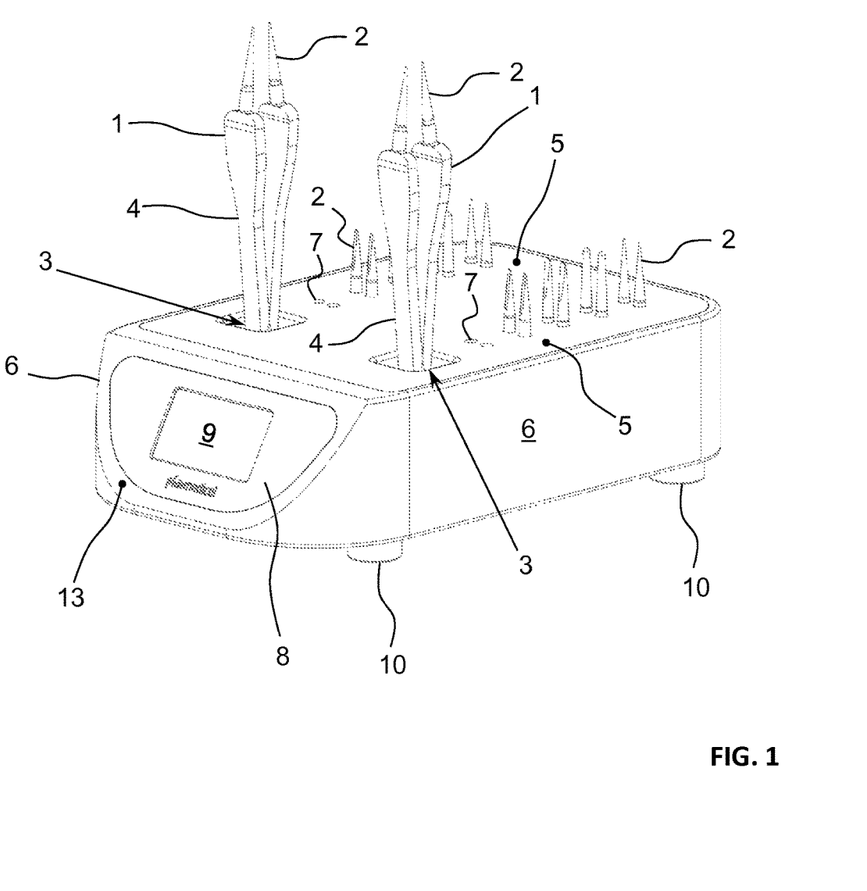
FIG. 1 a schematic view of an exemplary embodiment of a device for providing two pairs of ready-to-use tweezers having exchangeable tips, the housing of said device comprising a display for displaying the operating mode of the station and the charge status of the tweezers, FIG. 2 a schematic view, at an angle from behind, of the subject matter of FIG. 1, FIG. 3 a schematic view from the front of the subject matter of FIG. 1, FIG. 4 a schematic view from behind of the subject matter of FIG. 1

FIG. 1 shows a schematic view of the device with two pairs of tweezers 1 in respective charging stations 3. Similarly to an electric toothbrush, the tweezers are furnished with an inductively chargeable battery which supplies electrical power to a heating device integrated in the tweezers 1. Heating elements which are not included in the drawing serve for controlling the temperature of the tips 2, whose ends may be inserted into the legs 4 of the tweezers in temperature-controlled receptacles or attachable on temperature-controlled retaining elements.

FIG. 1 clearly shows that the charging station 3 is incorporated in the surface 5 of the housing, so that the tweezers 1 can be securely inserted into the charging station 3. The secure retaining of tweezers 1 is guaranteed.

FIG. 1 also shows that additional recesses 7 are provided in the surface 5 of the housing 6, which serve for the insertion of tips 2 in pairs. Tips 2 of various shapes can thus be stored, which can be assembled on the tweezers 1 by exchanging tips. The tips 2 are heated according to the general description.

The housing 6 is distinguished by a harmonious round shape and by an operating surface 8 provided on the front which is angled upward in order to facilitate handling by the user. A display 9, which can be designed as a touch panel, is integrated into the operating surface 8. In this case, there are no edges/joints provided leading into the housing 6, so the housing 6 can be constructed hermetically sealed. The housing 6 can consist of aluminum or plastic, preferably identically on all sides, although different colors and/or surface coatings are possible.

FIG. 1 further shows that the housing 6 stands on a total of four rubber feet 10, which enable the housing 6 to stand safely at a remove from the underlying surface.

Figure 2:
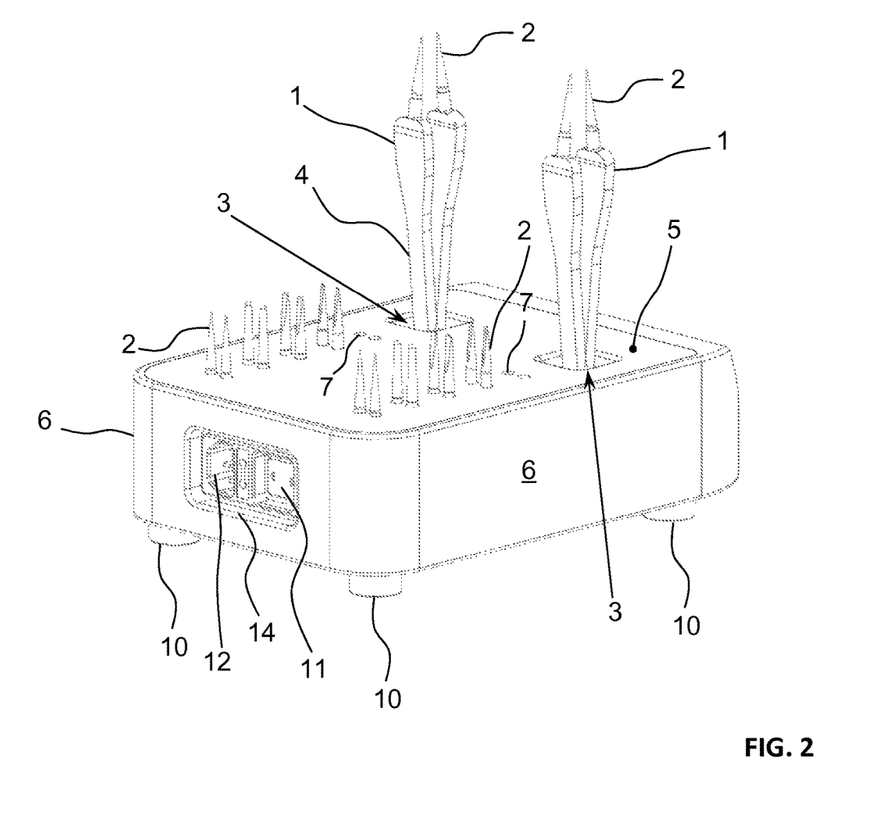

FIG. 2 shows the device from FIG. 1 in a schematic view, at an angle from behind, giving an overall impression in conjunction with the representation according to FIG. 1. An on/off switch 11 is provided on the back, which is recessed in the housing in order to prevent accidental engagement. Furthermore, a socket 12 is provided for inserting a plug for a high-voltage connection.

Figure 3:
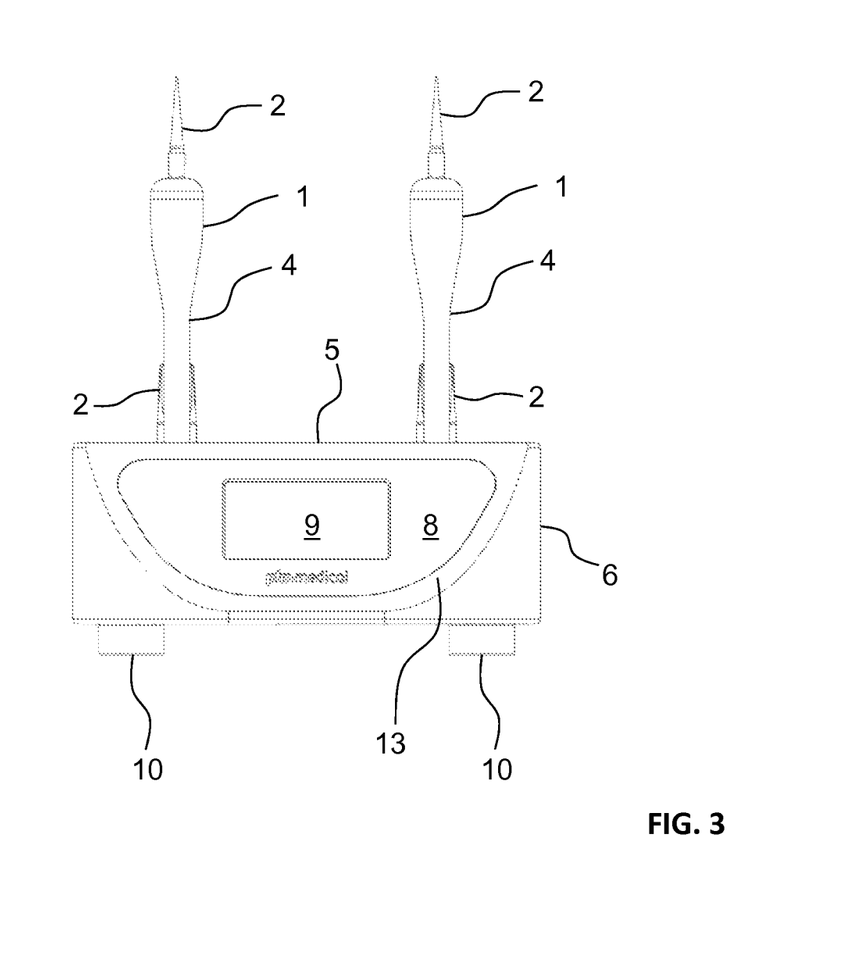

FIG. 3 shows the object from FIG. 1 in a frontal view showing the shape of the tweezers 1 in the region of legs 4.

The display 9 and the surface 13 serving for the integration of the display 9 are harmoniously matched but can also be designed differently.

Figure 4:
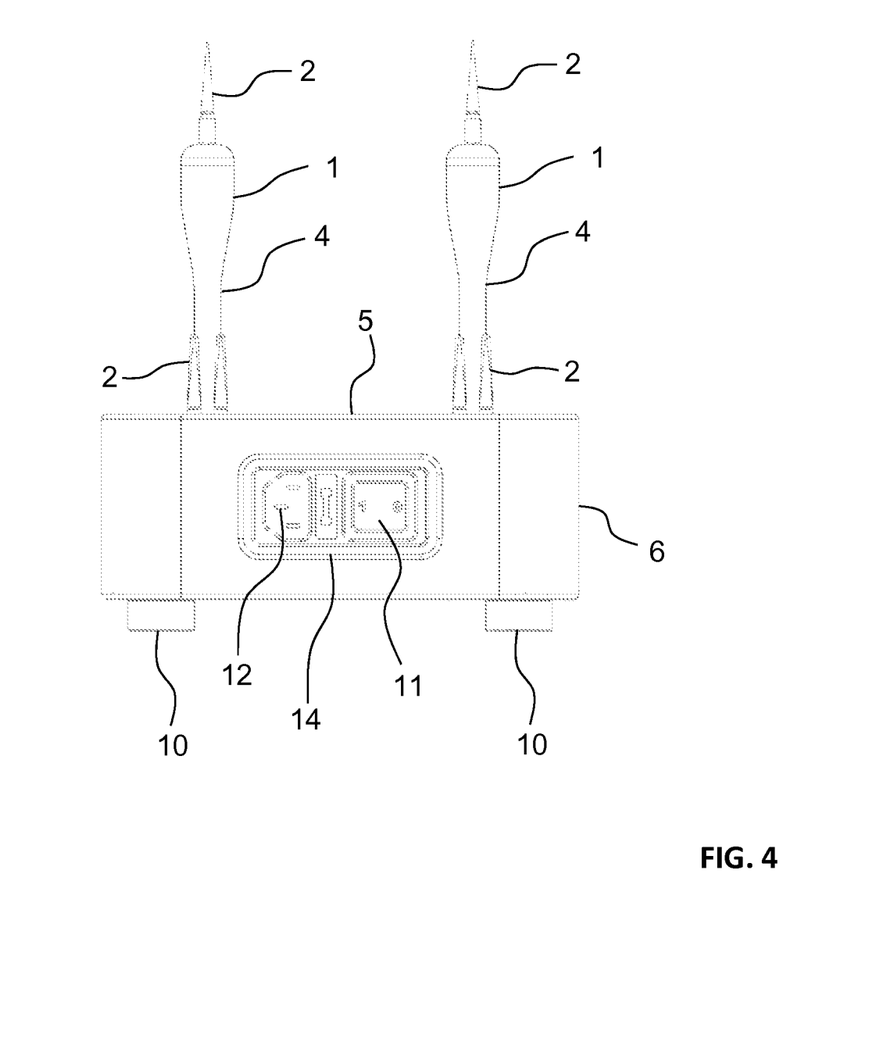

FIG. 4 shows the device from FIG. 1 from the back with the on/off switch 11 and the socket 12. The two are integrated in a switch frame 14.

Figure 5:
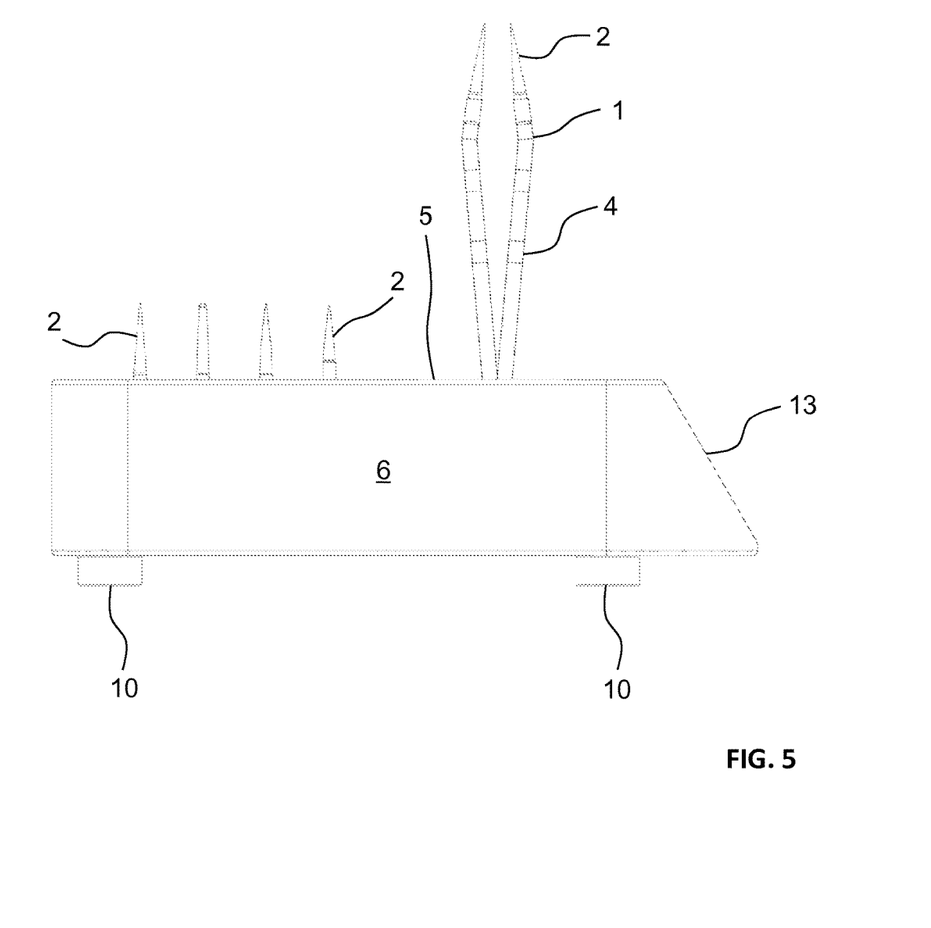
FIG. 5 a first schematic side view of the subject matter of FIG. 1.
Figure 6:
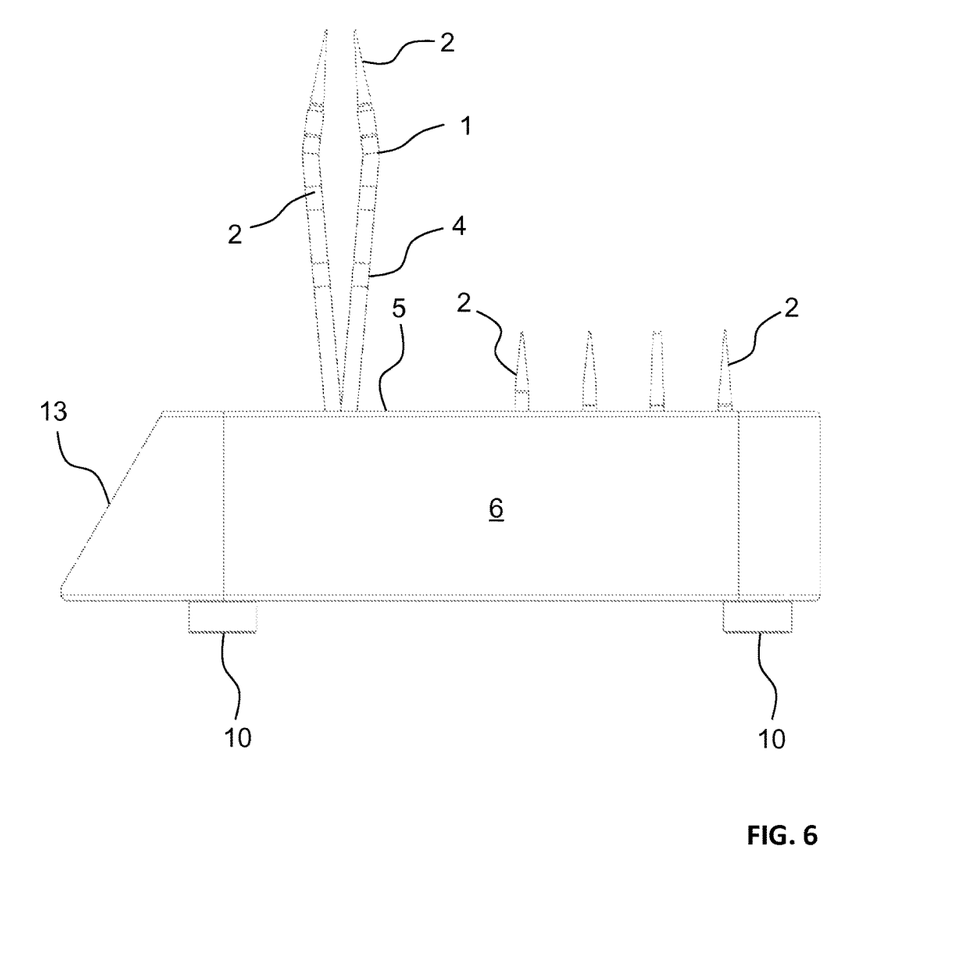
FIG. 6 a second schematic side view of the subject matter of FIG. 1 from the other side, FIG. 7 a schematic top view of the subject matter of FIG. 1 from above, and FIG. 8 a schematic view from below of the subject matter of FIG. 1.

FIGS. 5 and 6 show the device from FIG. 1 from the side, from which it clearly emerges that the housing 6 has no disruptive elements in the side wall whatsoever. To the contrary, the housing 6 is constructed smooth with a uniform surface. FIGS. 5 and 6 show the tweezers 1 placed there for charging and the course of the legs 4 from the side with tips 2 inserted. The stored tips 2 are also clearly visible.

Figure 7:
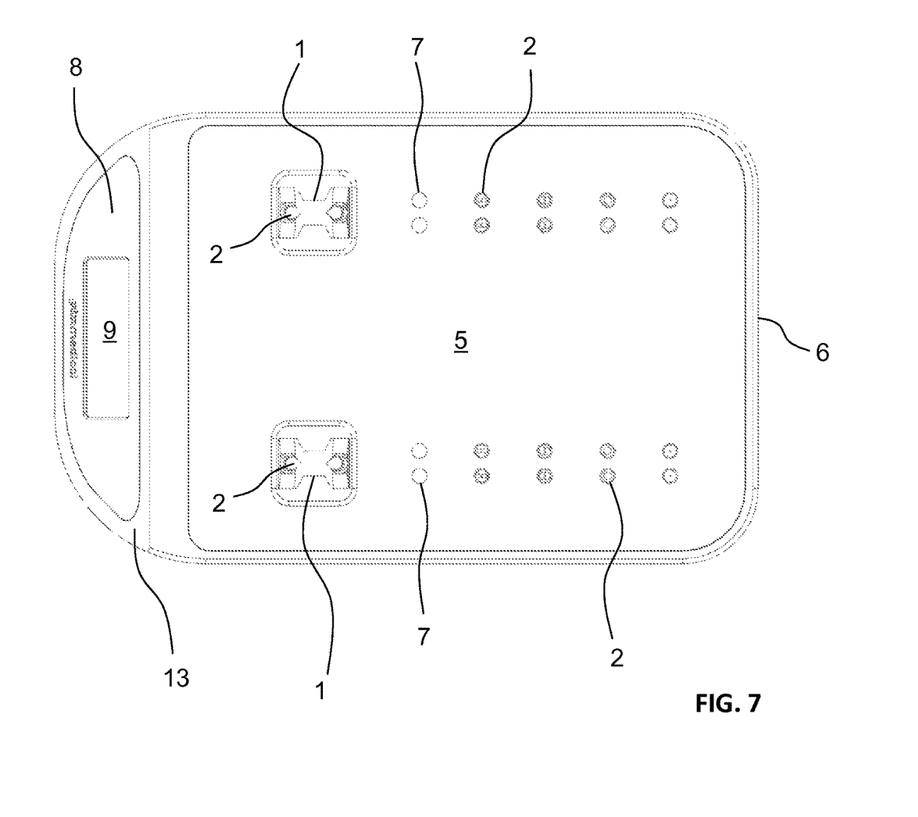

FIG. 7 shows the object from FIG. 1 in a top view wherein the surface 5 for placing tweezers 1 and tips 2 and the surface 13 with integrated display 9 are visible.

Figure 8:
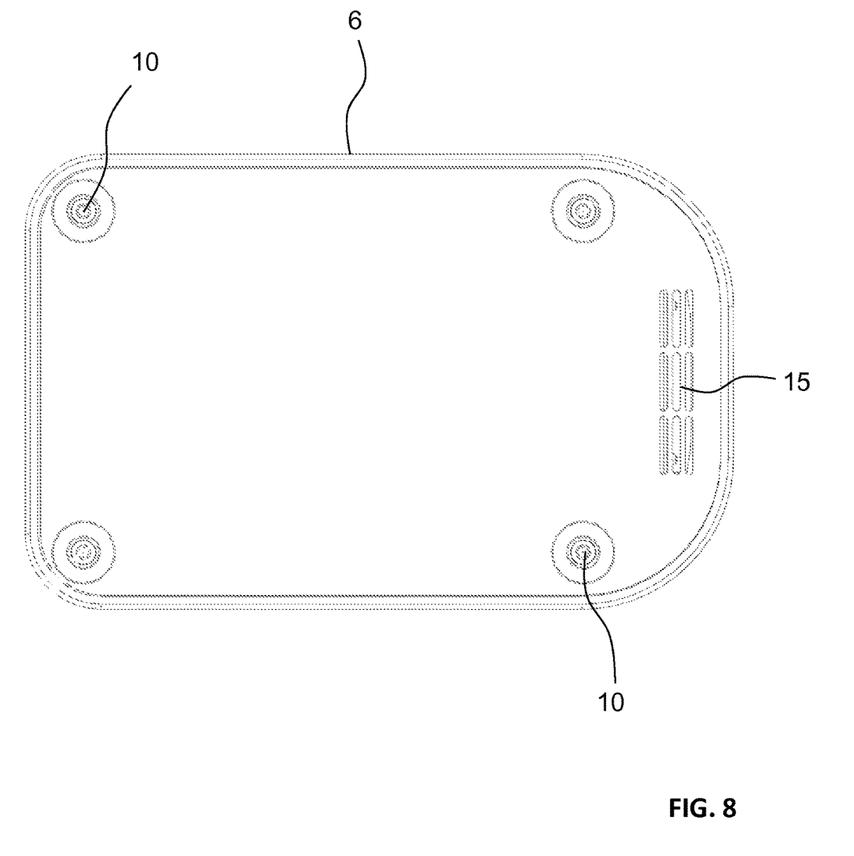

Finally, FIG. 8 shows the subject matter of FIG. 1 from below. The rubber feet 10 for securely positioning the device are visible. Ventilation slits 15 are also provided, although they are not required. It is conceivable that heat which arises inside the housing 6 could be emitted via the housing as long as the housing possessed sufficient thermal conductivity.

The tweezers according to the invention are characterized in that the tips and/or the joint region of the legs are designed as a housing with a storage medium for storing power, and that the storage medium directly or indirectly heats the engagement region, i.e. the tips, to a predetermined temperature.

The invention recognizes that it is advantageous to provide tweezers with a predetermined, in other words specifiable, constant temperature. To that end, the tweezers are furnished with a storage medium for storing power, said storage medium directly or indirectly heating the engagement region, i.e. the tips, of the two legs to a predetermined temperature and maintaining this temperature.

The storage medium can be integrated into the legs and/or the joint region of the legs at one end thereof, making it possible to use the entire available volume. Accordingly, the legs and the joint region, i.e. the entire body of the tweezers, can be constructed as a housing with the storage medium located inside the housing.

The storage medium can, for instance, be a heat store which is heated through direct thermal coupling. The housing has a thermally insulating character, so that the heat is expelled almost exclusively via the tips. Accordingly, the heat storage capacity of the material can be optimally exploited.

In a particularly advantageous development of the invention, the storage medium is an electrical power store which feeds an electrical heating unit which acts upon the engagement region, i.e. the tips. It is also expedient when the heating unit is a resistance heater which is in thermally conductive contact with the engagement region, i.e. the tips.

The resistance heater can comprise a special heating element, for instance a heating wire, heating coil, heating jacket, heating pad or heating cartridge. The ends of the tips are inserted into the heating element, creating thermally conductive contact between the heating element and the tips.

The electrical power store can be constructed as a battery or capacitor or capacitor arrangement. What is essential is that electrical power is stored, similarly to an electric toothbrush, where the power storage device, specifically a battery, is inductively charged when placed in a charging station. Regarding the construction of such a charging station, the features of the device claims will be laid out herein below.

According to a further advantageous embodiment, a control is provided for heating the engagement region to a predetermined or predeterminable, i.e. settable, temperature. This control can comprise a kind of power management, namely in order to realize an optimal tweezer temperature control for an optimally long time period with a predetermined amount of power. The temperature of the tips can conceivably be adjustable within a given range, with the control enabling the optimal use of the available power. To this end, it is essential that the heated region actually be concentrated only at the tips, so that they can be held at body temperature, for instance, using the lowest possible amount of power. The tips should be made of a metal with a high thermal conductivity and a large heat storage capacity. It is also conceivable for the tips to be coated, preferably with a thermally conductive material such as titanium or a titanium alloy, regardless of the base material. The coating material should be hard and robust, namely in order to reduce wear and tear. The tips can be designed more robust this way.

It is also expedient that the legs or the housing thereof are produced from plastic and/or ceramic. As mentioned above, the housing should have thermally insulating properties. On the exterior, measures can be taken to improve the haptics of the housing, or respectively the legs, such as by providing knobs, grooves, or the like, namely measures which facilitate handling.

It must be noted here that the tweezers constructed as described above must contain all the elements necessary for power transmission and heating of the tips, in a manner similar to an electric toothbrush with regard to kinetics. The battery is usually charged inductively just as with the electric toothbrush. The further description of those electrical/electronic elements and modules can be dispensed with; reference is made to similarly functioning devices.

The engagement region forming the tips of the tweezers, i.e. the tips, can be exchangeable in pairs so that the tweezers are universally usable. The exchangeable free ends of the legs, namely the tips, can be connected to the leg stumps by friction and/or interlockingly, in particular via a plug connection, snap connection, screw connection, or bayonet connection. Easy tip exchange simplifies handling significantly. For instance, flat "tips" can be effortlessly replaced with claw-shaped tips of any shape as needed. The tweezers can also be repurposed as a cutting/punching device by changing the tips appropriately.

As mentioned above, in one tweezer configuration, similarly to an electric toothbrush, an electrical charging station is provided, particularly for inductively charging the power storage device provided in the tweezer body. This can automatically supply an integral heating device with electrical power. An external power supply can also directly supply the internal, i.e. integral, heating device, namely when the tweezers are situated in a corresponding charging station.

It is also conceivable for a switch to be provided at a tweezer leg, for instance, for the purpose of activating the heating device, so that heating begins when the tweezers are turned on.

With reference to a device, the above-stated objective is attained by the features of the broadest device-based claim provided herein. According to this claim, a device for providing at least one usable pair of tweezers according to the embodiments described above is characterized by a housing which forms a station and, constructed in the housing, preferably on the top, a region for insertion/placement/attachment, which serves for positioning and charging the tweezers. The tweezers are preferably charged in an upright position, i.e. vertically, similarly to an electric toothbrush. It is also conceivable for the tweezers to be placed in a charging bay constructed in the housing, in which case the inductive coupling occurs in the known manner given such positioning.

With regard to working continuously with temperature-controlled tweezers, it is also expedient when the housing comprises two regions for inserting/placing/attaching two independent pairs of tweezers. Thus the first pair of tweezers can be used in a fully charged and heated condition until the electrical power for heating the tips and holding them at a predetermined temperature level is used up. In order to determine when that happens, the temperature in the tips can be detected by means of a temperature sensor which emits a signal via a corresponding processor directly to the tweezers or over a contactless connection via the station. When the tweezer battery charge status is no longer sufficient, the user can place it in the charging station and use the second pair of tweezers. The first pair of tweezers will recharge during this time. Special electronics for rapid charging can be provided.

As already stated above, the insertion/placement/attachment regions are constructed as inductively functioning charging stations, in which case the tweezers can comprise a hermetic housing which eliminates as far as possible the risk of damage due to improper handling. Accordingly, the station housing is equipped with a continuous surface regardless of the respective contour, so that the station does not pose any risks either. In addition, this design allows the surfaces to be cleaned much more easily.

As described above, the tips of the respective tweezers are exchangeable, preferably in pairs. Accordingly, it is expedient that the housing comprises a plurality of receptacles, particularly insertion openings or attachment pins, for providing pairs of tips with a variety of shapes. They can be provided adjacent one another either in an upright position, sticking out, or recumbent position, namely in duplicate, as long as the station comprises two pairs of tweezers.

It is also expedient that the tips/pairs of tips are provided in the heated and temperature-controlled condition. For the purpose of heating the receptacles, or respectively the pairs of tips located therein, a special heating device can be provided, which is either constructed as a resistance heater or inductively connected directly to the tip material. This measure benefits the power management of the power storage device in the tweezers, especially since it is unnecessary to heat up a pair of replacement tips from a low temperature at which they are provided to a temperature corresponding to body temperature, for instance.

The same applies to the provision of the tweezers themselves. As long as the tweezers are in the charging station, the tip temperature control process can already be activated, so that the tweezers are provided with temperature-controlled tips. All these functions can be activated by means of a control panel, preferably a touch panel, which is preferably allocated to the display. Film-protected switches which are integrated into the display area can also be provided.

As mentioned above, the housing comprises a display, which is preferably integrated into a front, upwardly inclined region of the housing. The display indicates the operating mode of the station and/or the charge status of the tweezers.

In a particularly refined manner, the connection between the station and the respective tweezers can be a wireless connection, preferably a Bluetooth connection, a connection via high-frequency signals, or a connection over a WLAN network, in which case integration in a computer system is also possible. It is also conceivable for the station to be controlled by means of an organizer with the aid of a separate program in the form of a so-called app.

The charge status/operating mode of the tweezers can conceivably also be displayable and potentially also communicable to the user visually and/or acoustically via the station by means of the display provided in the housing there. That way, the user has the ability while at the station to determine, or at least estimate, how long he can continue to use the tweezers with sufficient temperature control. If necessary, he will then return the tweezers to the charging station and use the second pair of tweezers which is being stored.

Through the interaction of the inventive device described above and the inventive tweezers described above, the heating of the tweezers, in which an internal heating device as well as a battery for storing electrical power are located, can proceed as follows:

The tweezers are located in the charging cradle, i.e. the insertion/placement/attachment region, and positioned there accordingly. In this condition the device, which holds at least one pair of tweezers, is switched on. As long as they are properly situated in the charging station, the tweezers are supplied directly with electrical power, and the electrical power, i.e. the current, does not flow from the battery of the tweezers. Rather, while the battery is bypassed, or while the battery is expediently charging, the tweezers are supplied with current directly, or more precisely the internal heating device of the tweezers is supplied with current directly, so that the tweezers, in particular their tips, are brought to operating temperature. The battery charging process occurs simultaneously.

When the tweezers are removed from the charging station, they, in particular their tips, are temperature-controlled by means of the internal battery of the tweezers.

As soon as the electrical power of the internal battery is used up, for instance after a period of 30 minutes, an acoustic signal or a visual signal such as a warning lamp is triggered, which notifies the user that the tweezers need to be placed in the charging station of the device again in order to recharge the battery. When the tweezers are back in the charging station again, the process repeats itself as described above; i.e., the internal heating device is supplied with power directly, and the tweezer tips are heated while the battery charges.

When two charging stations and correspondingly at least two pairs of tweezers are provided, the second pair of tweezers is available "charged"; i.e., the tweezer tips are at operating temperature, and the second tweezers' battery is "full". This second pair of tweezers can be used while the first pair of tweezers undergoes the charging process—the heating of the tweezer tips through a direct power supply and the charging of the battery.

During the charging process the device, i.e. the charging station, takes over the power supply until the desired temperature is reached in the tweezer tips. If necessary the tweezers can then be exchanged, so that the provision of at least two tweezers enables continuous work.

It is generally also conceivable for the temperature of the tweezers, i.e. their tips, to be controlled by means of the charging station directly without an internal heating device being provided in the tweezers. In this case, given the provision of a corresponding heat accumulator, the tweezers would be charged thermally and could be used for as long as the heat accumulator supplied sufficient heat to the tweezer tips to keep them at operating temperature. An alarm could be emitted when the temperature fell below the operating temperature, so that the first pair of tweezers, whose heat accumulator was no longer sufficiently "full", could be exchanged for the second pair of tweezers, which was thermally charged up.

Finally, explicit reference is made to the fact that the exemplary embodiments of the device according to the invention described above are used only for explanation of the claimed teaching, but the teaching is not restricted to the exemplary embodiments.

REFERENCE LIST 1 tweezers
2 tip
3 charging station
4 leg (of the tweezers)
5 surface (for tweezer placement)
6 housing (insertion opening)
7 recess (in the surface 5)
8 operating surface
9 display (in the operating surface)
10 rubber foot
11 on/off switch
12 socket
13 surface (for display)
14 switch frame
15 ventilation slits

The invention claimed is:

1. Tweezers (1) for handling histological preparations, said tweezers comprising:
   two legs (4) which are joined elastically at one end of each of the two legs (4) and define a joint region;
   tips (2) constructed on the opposing free ends of each of the two the legs (4) and defining an engagement region; and
   a central region located intermediate the joint region and the engagement region, the central region serving for holding and actuating the legs (4) for the purpose of bringing the tips (2) into contact with each other,
   wherein:
      at least one of the tips (2) or the joint region are constructed as a housing (6) comprising a storage medium for storing power,
      the storage medium at least one of directly or indirectly heats the engagement region to a predetermined temperature,
      the housing (6) has thermally insulating properties,
      the storage medium is either a heat accumulator or an electrical power storage device configured as an electrical heating device, wherein the storage medium acts upon the engagement region and is in thermally conductive contact with the engagement region,
      a charging station (3) is operatively attachable to the tweezers (1) and configured for positioning the tweezers and for at least one of inductive charging of energy storage or for direct power supply of an internal heating device,
      at least one of the inductive charging or the direct power supply occurs when the tweezers (1) are positioned in the charging station (3), and
      the engagement region forming the tip (2) is exchangeable in tip pairs of different shapes.

2. Tweezers according to claim 1, wherein the histological preparations are thin tissue samples.

3. Tweezers according to claim 1, wherein the electrical heating device is a resistance heating device.

4. Tweezers according to claim 3, wherein the resistance heating device comprises as a heating element at least one of a heating wire, a heating coil, a heating jacket, a heating pad or a heating cartridge.

5. Tweezers according to claim 1, wherein the electrical power storage device is at least one of a battery or a capacitor.

6. Tweezers according to claim 1, wherein a control is provided for the purpose of heating the engagement region to a predetermined temperature.

7. Tweezers according to claim 1, wherein a control is provided for the purpose of heating the engagement region to a selectable temperature.

8. Tweezers according to claim 1, wherein the tips (2) are made of metal.

9. Tweezers according to claim 1, wherein the tips, regardless of the base material, are coated with at least one of a thermally conductive or a hard material.

10. Tweezers according to claim 9, wherein the tips are coated with titanium or a titanium alloy.

11. Tweezers according to claim 1, wherein at least one of the legs (4) or the housing (6) is made of plastic.

12. Tweezers according to claim 1, wherein at least one of the legs (4) or the housing (6) is made of ceramic.

13. Tweezers according to claim 1, wherein the exchangeable free ends of the legs (4) are connectable to the legs (4) by at least one of friction and an interlocking means.

14. Tweezers according to claim 13, wherein interlocking means comprise at least one of a plug connection, a snap connection, a screw connection or a bayonet connection.

15. Device for providing at least one ready-to-use pair of tweezers (1) according to claim 1, wherein:
   the charging station (3) defines an insertion/placement/attachment region that is constructed in either the housing (6) on or in the top side (5), the insertion/placement/attachment region being configured to facilitate for vertical positioning and charging of at least one of the pair of tweezers (1);
   the housing (6) has a plurality of receptacles for providing pairs of variably shaped tips.

16. Device according to claim 15, wherein the housing (6) has two insertion/placement/attachment regions for receipt of two pairs of tweezers (1).

17. Device according to claim 15, wherein the plurality of receptacles comprise insertion openings (7) or contact pins for providing pairs of variably shaped tips.

18. Device according to claim 15, wherein a heating device is provided for heating the receptacles and the pairs of tips therein, the heating device being constructed as either a resistance heating device or as being inductively coupled directly to the tips.

19. Device according to claim 15, wherein the housing (6) comprises a display (9) which shows at least one of the operating mode of the station (3) or the charge status of the tweezers (1).

20. Device according to claim 15, wherein the display is in a front region of the device, the front region being angled.

21. Device according to claim 15, further comprising a wireless connection between the station (3) and the tweezers via which the charge status/operating mode of the tweezers (1) is transmitted to the station (3).

22. Device according to claim 21, wherein the wireless connection between the station (3) and the tweezers is a Bluetooth connection.

23. Device according to claim 21, wherein the charge status/operating mode of the tweezers (1) transmitted to the station (3) is indicated at least one of visually or acoustically.

* * * * *

UNITED STATES PATENT AND TRADEMARK OFFICE
CERTIFICATE OF CORRECTION

PATENT NO. : 10,046,327 B2
APPLICATION NO. : 15/302577
DATED : August 14, 2018
INVENTOR(S) : Schneider et al.

Page 1 of 1

It is certified that error appears in the above-identified patent and that said Letters Patent is hereby corrected as shown below:

In the Claims

Column 12,
Line 27, "connectable" should read --connectible--.

Signed and Sealed this
Thirtieth Day of October, 2018

Andrei Iancu
*Director of the United States Patent and Trademark Office*